United States Patent
Tai et al.

(10) Patent No.: US 10,195,238 B2
(45) Date of Patent: Feb. 5, 2019

(54) COMPOSITION FOR INHIBITING RENAL CANCER CELL GROWTH AND ENHANCING KIDNEY FUNCTION

(71) Applicants: TAIWAN INDIGENA BOTANICA CO., LTD., Taipei (TW); TAIPEI MEDICAL UNIVERSITY, Taipei (TW)

(72) Inventors: Cheng-Jeng Tai, Taipei (TW); Yeu-Ching Shi, New Taipei (TW); Ching-Hua Su, Taipei (TW)

(73) Assignees: TAIWAN INDIGENA BOTANICA CO., LTD., Taipei (TW); TAIPEI MEDICAL UNIVERSITY, Taipei (TW)

( * ) Notice: Subject to any disclaimer, the term of this patent is extended or adjusted under 35 U.S.C. 154(b) by 0 days.

(21) Appl. No.: 15/406,786

(22) Filed: Jan. 16, 2017

(65) Prior Publication Data
US 2017/0224752 A1  Aug. 10, 2017

(30) Foreign Application Priority Data
Feb. 5, 2016  (TW) .............................. 105104036 A

(51) Int. Cl.
| | | |
|---|---|---|
| *A61K 36/074* | (2006.01) | |
| *A61K 9/20* | (2006.01) | |
| *A61K 31/122* | (2006.01) | |
| *A61K 31/7076* | (2006.01) | |
| *A61K 36/07* | (2006.01) | |

(52) U.S. Cl.
CPC .......... *A61K 36/074* (2013.01); *A61K 9/2013* (2013.01); *A61K 9/2031* (2013.01); *A61K 9/2054* (2013.01); *A61K 31/122* (2013.01); *A61K 31/7076* (2013.01); *A61K 36/07* (2013.01)

(58) Field of Classification Search
None
See application file for complete search history.

(56) References Cited

U.S. PATENT DOCUMENTS

| | | | | |
|---|---|---|---|---|
| 6,558,943 B1 * | 5/2003 | Li | ............................ | C12N 1/14 424/93.5 |
| 7,135,183 B1 * | 11/2006 | Wang | ................... | A61K 36/074 424/195.15 |
| 2014/0066498 A1 * | 3/2014 | Wu | ....................... | C07D 317/64 514/456 |
| 2016/0339054 A1 * | 11/2016 | Lai | ....................... | A61K 31/715 |
| 2017/0035820 A1 * | 2/2017 | Stamets | ................. | A61K 36/07 |
| 2017/0368119 A1 * | 12/2017 | Wu | ....................... | A61K 38/168 |

OTHER PUBLICATIONS

Popovic V. et al. Mycotherapy of Cancer. Current Topics in Medicinal Chemistry 13:2791-2806. (Year: 2013).*
Lee, T. et al. A New Cytotoxic Agent from Solid State Fermented Mycelium of A. camphorata. Planta Medica 73*13)1412-1415. (Year: 2007).*
Sliva, D. Cellular and Physiological Effects of G. lucidum. Mini Reviews in Medicinal Chemistry 4(8)873-879. (Year: 2004).*
Wang, C. et al. Ethanolic Extract of T. camphoratus . . . Integrative Medicine Research 4(1)Suppl 1 p. 49, Abstract P1.021 May 2015. (Year: 2015).*

* cited by examiner

*Primary Examiner* — Ralph J Gitomer
(74) *Attorney, Agent, or Firm* — Anova Law Group, PLLC

(57) ABSTRACT

The present invention provides a composition for inhibiting renal cancer cell growth and enhancing kidney function. This composition is constituted of water-soluble base material, plasticity-increasing base material, *Antrodia camphorata* extract, *Ganoderma lucidum* extract, and auxiliary enzyme. Differing from the conventional therapeutics treating the glomerulonephritis by administering high-dosage steroid for 1-4 months, the renal function of a patient suffering with serious kidney failure can be obviously enhanced after administering this composition of 7 mg/day/kg to the patient for 20 days. Moreover, because the cell biological experiments have proved that the of the present invention possess the functionality to inhibit renal cancer cell growth, this novel composition can indeed be used with chemotherapy drugs clinically, so as to solve the issue that the chemotherapy drugs cannot effectively inhibit the renal cancer cell growth.

8 Claims, 2 Drawing Sheets

COMPOSITION FOR INHIBITING RENAL CANCER CELL GROWTH AND ENHANCING KIDNEY FUNCTION

BACKGROUND OF THE INVENTION

1. Field of the Invention

The present invention relates to the technology field of medically-used composition, and more particularly to a composition for inhibiting renal cancer cell growth and enhancing kidney function.

2. Description of the Prior Art

Kidneys locate at the rear of the abdominal cavity in the retroperitoneal space, and consist of a left kidney and a right kidney. One normal kidney contains 800,000 to 1.5 million nephrons, wherein the nephron is mainly constituted by a glomerular, a bowman's capsule and renal tubules. Kidney plays an important role in circulation and excretion systems of human body, which includes following functions:
(1) excreting wastes or remaining drugs in human body;
(2) regulating electrolytes and maintaining the salt and water balance in human body;
(3) producing vasopressin to control blood pressure;
(4) producing vitamin D to control absorption of calcium and growth of bone;
(5) producing erythropoietin to maintain the normal metabolism of erythrocyte.

Because kidney is an indispensable organ in human body, the wastes, the remaining drugs and the metabolites produced by circulation system cannot be eliminated from human body normally as the kidney works abnormally. To be more serious, the kidney failure may lead to others companion diseases such as uremia.

Adrenal cortical hormone, also called steroid, is a prescription medicine conventionally used for treating glomerular inflammation and nephrotic syndrome. However, the treatment effect will obviously present only if the high-dosage steroid is administered to the patient for 1-4 months. Moreover, it is well know that, long term administration of the steroid would induce some side effects, such as high blood glucose, moon face, buffalo shoulder, emotional instability, and abnormal adrenal hormone.

On the other hand, kidney carcinoma is one kind of tumor with high malignancy, and can be divided into renal cell carcinoma (RCC), renal pelvis carcinoma, and renal adenocarcinoma. Renal adenocarcinoma is derived from pathologically-changing tubular epithelial cells, and occurs mostly on an adult. Moreover, it is frightening that the renal cell carcinoma (RCC) will not reveal any obvious early symptoms; instead of that, symptoms of pain and hematuria would present after the tumor cells diffuse to the organs adjacent to the kidney.

Therapies for the RCC are divided into surgical therapy, chemotherapy, radiation therapy, and immunotherapy. Recently, to cure the RCC, doctors usually excises the renal tumor portion of the kidney through the surgical therapy and then subsequently treating the RCC by using immunotherapy. By such way, the patient suffering from the RCC is able to reserve more kidney function. However, despite the doctors administer uses target drugs such as Sutent and Nexavar to the kidney cancer patient for inhibiting the growth of tumor cells, the tumor cells' rapid and serious growth cause the target drugs unable to show an ideal therapy effect on the tumor cells. In addition, long term administration of the above-mentioned two target drugs would induce some side effects, such as hand-foot syndrome, skin hyperplasia, diarrhea, fatigue, and skin peeling.

Thus, because the conventionally-used prescription medicine (i.e., the steroid) for treating glomerular inflammation and nephrotic syndrome and the targets drugs for inhibiting the growth of renal tumor cells may cause side effects to kidney cancer patients, the inventor of the present application has made great efforts to make inventive research thereon and eventually provided a composition for inhibiting renal cancer cell growth and enhancing kidney function.

SUMMARY OF THE INVENTION

The primary objective of the present invention is to provide a composition for inhibiting renal cancer cell growth and enhancing kidney function. This novel composition is constituted of water-soluble base material, plasticity-increasing base material, *Antrodia camphorata* extract, *Ganoderma lucidum* extract, and auxiliary enzyme. Differing from the conventional therapeutics treating the glomerulonephritis by administering high-dosage steroid for 1-4 months, the renal function of a patient suffering with serious kidney failure can be obviously enhanced after administering this composition of 7 mg/day/kg to the patient for 20 days. Moreover, because the cell biological experiments have proved that the composition of the present invention possess the functionality to inhibit renal cancer cell growth, this novel composition can indeed be used with chemotherapy drugs clinically, so as to solve the issue that the chemotherapy drugs cannot effectively inhibit the renal cancer cell growth.

In order to achieve the primary objective of the present invention, the inventor of the present invention provides an embodiment of the composition for inhibiting renal cancer cell growth and enhancing kidney function, comprising:
a first substrate, having a first weight percent in a range from 40 wt % to 60 wt %;
a second substrate, having a second weight percent in a range from 5 wt % to 10 wt %;
an *Antrodia camphorata* extract, having a third weight percent in a range from 8 wt % to 15.5 wt %;
a *Ganoderma lucidum* extract, having a fourth weight percent in a range from 18 wt % to 34 wt %; and
a first coenzyme, having a fifth weight percent in a range from 1.5 wt % to 3.1 wt %; and
wherein after administering the composition with an adult dosage of at least 3 mg/day/kg, the cell viability of kidney cancer cells is reduced an below 30%;
wherein a daily dosage of the composition for a renal failure patient to regulate blood urea nitrogen (BUN) and creatinine (Cr) is at least 3 mg/day/kg.

According to the aforesaid embodiment of the composition for inhibiting renal cancer cell growth and enhancing kidney function, wherein the first substrate is a water-soluble base material selected from the group consisting of: polyethylene glycol (PEG), polyvinylpyrrolidone (PVP), polyoxyethylene monostearate (S40), sodium stearate, glycerin, gelatin, urea, poloxamer, and combination of the aforesaid two or more materials.

According to the aforesaid embodiment of the composition for inhibiting renal cancer cell growth and enhancing kidney function, wherein the second substrate is a plasticity-increasing base material selected from the group consisting of: pre-gelatinized starch, carboxymethyl starch, methylcellulose, sodium carboxymethyl cellulose, hydroxypropyl methylcellulose, acacia, alginic acid, dextrin, cyclodextrin, agar, lactose, and combination of the aforesaid two or more materials.

According to the aforesaid embodiment of the composition for inhibiting renal cancer cell growth and enhancing kidney function, wherein the *Antrodia camphorata* extract at least comprises triterpenoids and adenosine, and the *Ganoderma lucidum* extract at least comprises polysaccharides.

BRIEF DESCRIPTION OF THE DRAWINGS

The invention as well as a preferred mode of use and advantages thereof will be best understood by referring to the following detailed description of an illustrative embodiment in conjunction with the accompanying drawings, wherein.

DETAILED DESCRIPTION OF THE PREFERRED EMBODIMENTS

Figure 1:
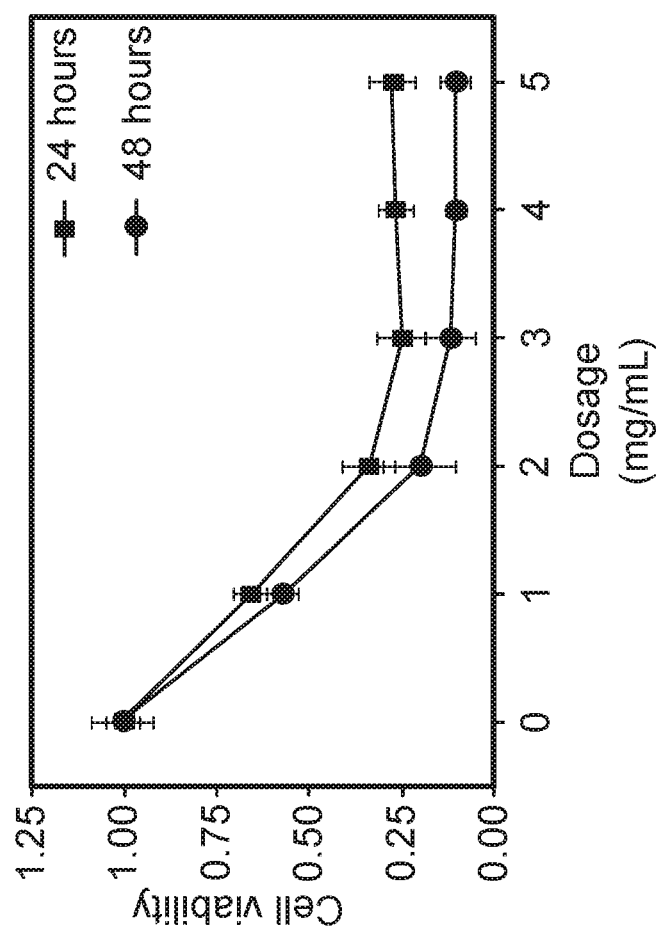
FIG. 1 shows two plot curves of dosage versus cell viability.

To more clearly describe a composition for inhibiting renal cancer cell growth and enhancing kidney function according to the present invention, embodiments of the present invention will be described in detail with reference to the attached drawings hereinafter.

This composition is fabricated through a solid dispersion process consisting of following processing steps:

step (1): mixing a water-soluble base material with a plasticity-increasing base material for obtaining a mixed base material, and then heating the mixed base material for further obtaining a melted substrate;

step (2): adding an *Antrodia camphorata* extract, a *Ganoderma lucidum* extract, and a first coenzyme into the melted substrate so as to obtain a fluid mixture;

step (3): evenly stirring the fluid mixture, and then transferring the fluid mixture to a reservoir bottle, so as to store the fluid mixture under 70-100° C.;

step (4): using a pill dropping machine to drop the fluid mixture into a condensing agent under 70-100° C., so as to make the dropped fluid mixture become a dripping pill in the condensing agent; and step (5): collecting a variety of dripping pills.

The collected dripping pills have a dripping pill with a specific pill size and a specific pill weight, wherein the specific pill size is in a range from 2.0 mm to 3.5 mm and the specific pill weight is in a range from 18 mg/pill to 25 mg/pill. Moreover, it needs to further explain that, the water-soluble base material used in the step (1) can be a polyethylene glycol (PEG), a polyvinylpyrrolidone (PVP), polyoxyethylene monostearate (S40), a sodium stearate, a glycerin, a gelatin, a urea, poloxamer, or a combination of the aforesaid two or more materials. In addition, the plasticity-increasing base material used in the step (1) can be a pre-gelatinized starch, a carboxymethyl starch, a methylcellulose, a sodium carboxymethyl cellulose, a hydroxypropyl methylcellulose, a acacia, a alginic acid, a dextrin, a cyclodextrin, an agar, a lactose, or a combination of the aforesaid two or more materials.

Moreover, the *Antrodia camphorata* extract used in the step (1) has a third weight percent in a range from 8 wt % to 15.5 wt %, and at least comprises compositions of triterpenoids and adenosine. On the other hand, the *Ganoderma lucidum* extract used in the step (1) has a third weight percent in a range from 18 wt % to 34 wt %, and at least comprises compositions of polysaccharides. Furthermore, the first coenzyme can be a B vitamin group or a ubiquinone, and has a fifth weight percent in a range from 1.5 wt % to 3.1 wt %.

Now referring to following Table 1, which records with the functional compositions of the collected dripping pill of the composition for inhibiting renal cancer cell growth and enhancing kidney function.

TABLE 1

| Ingredients | Pharmacological effects |
| --- | --- |
| Triterpenoids | inhibiting the release of histamine, stimulating liver functions, and anti-inflammation |
| Adenosine | inhibiting the aggregation of platelet and improving blood circulation |
| Polysaccharides | immune modulation and anti-allergy |
| B vitamin group | dissipating fatigue |

It is able to further add a second coenzyme into the fluid mixture during the step (2), so as to enhance or increase the pharmacological effects of the dripping pill of the composition. In which, the second coenzyme can be a B vitamin group or a ubiquinone, and has a fifth weight percent in a range from 1.5 wt % to 3.1 wt %. Moreover, it is well know that the ubiquinone includes the pharmacological effects of: strengthening immunity and antioxidant capacity, slowing aging, and enhancing human vitality. So that, since the dripping pill of the composition includes many pharmacological effects, the dripping pill can provides health benefits to users' cardiovascular system and renal function.

Preferred Embodiment

A preferred embodiment is deigned and provided for verifying the medical efficacies and pharmacological effects of the composition in following paragraphs, wherein the constituting ingredients of the preferred embodiment of the composition is listed in following Table 2.

TABLE 2

| Ingredients | Formula |
| --- | --- |
| water-soluble base material | 45 wt % polyethylene glycol + 5 wt % sodium stearate |
| plasticity-increasing base material | 5 wt % hydroxypropyl methylcellulose |
| Antrodia camphorata extract | 12.5 wt % |
| Ganoderma lucidum extract | 27.5 wt % |
| B vitamin group | 2.5 wt % |
| coenzyme Q10 | 2.5 wt % |

The composition is processed to a dripping pill with a grain size of 3.0 mm. Moreover, inventors of the present invention use the composition with a daily dosage of at least 3 mg/day/kg to finish a clinical trial. The object in the clinical trial is a bladder cancer patient simultaneously suffering with renal failure. The patient has been unable to urinate easily and normally since being admitted to hospital in July, 2015. Following Table 3 has recorded with blood urea nitrogen (BUN) and creatinine (Cr) data of the patient.

TABLE 3

| | Test item | |
|---|---|---|
| Date | BUN (mg/dl) normal level: 7-20 mg/dl | Cr (mg/dl) normal level: 0.6-1.2 mg/dl |
| 2015 Jul. 22 | 89.5 | 5.1 |
| 2015 Aug. 3 | 90.7 | 5.5 |
| 2015 Aug. 24 | 149.5 | 4.9 |
| 2015 Aug. 8 | 106.5 | 3.5 |
| 2015 Sep. 4 | 100.8 | 2.6 |

As medically personnel knows, renal failure would cause the patient suffering from oliguria (defined as a urine output that is less than 400 mL daily in adults). Moreover, because the wastes in the body of the renal failure patient is difficult to be excreted, the renal failure patient may also suffer from some complications, such as acidosis, hyperkalemia, hypocalcemia, hyperphosphatemia, and anemia. The value of glomerular filtration rate (GFR) is generally used for judging whether an adult suffers from renal failure or not, wherein the GFR can be measured through the change of urine volume and the waste concentration in blood. Therefore, from above-presented Table 3, it can find that the renal failure of the inpatient does not be improve although the patient has been undergone the immunotherapy treatment for 2 months.

So that, attending doctor starts to administer the composition with a daily dosage of 7 mg/day/kg to the patient from September, 2015. Therefore, the renal failure patient is able to urinate after receiving such treatment for 20 days. Following Table 4 has recorded with BUN and Cr data of the renal failure patient.

TABLE 4

| | Test item | |
|---|---|---|
| Date | BUN (mg/dl) normal level: 7-20 mg/dl | Cr (mg/dl) normal level: 0.6-1.2 mg/dl |
| 2015 Sep. 24 | 30.6 | 1.7 |
| 2015 Oct. 8 | 52.0 | 1.5 |
| 2015 Nov. 19 | 39.3 | 1.7 |

Comparing to the BUN (100.8 mg/dl) and Cr (2.6 mg/dl) data measured on Sep. 4, 2015, the BUN and Cr level of the renal failure patient are respectively lowered to 30.6 mg/dl and 1.7 mg/dl after administering the composition with 7 mg/day/kg daily dosage to the patient for 20 days. That is, the clinical trial data have proved that the composition proposed by the present invention indeed can enhance kidney function.

Furthermore, in order to verify whether the composition possesses the functionality to inhibit renal cancer cell growth or not, the inventors of the present invention has completed a cell biological experiment. The cell biological experiment includes a control (Col) group and an experiment (Exp) group.

In the group Col, human embryonic kidney cells 293T (HEK293T cells) are placed into a 96-well microplate for making the 96-well microplate carries with $1\times10^4$ cell/well HEK293T cells. Moreover, the HEK293T cells in the 96-well microplate are treated with water for 24 hours and 48 hours, respectively.

In the group Exp, human embryonic kidney cells 293T (HEK293T cells) are placed into a 96-well microplate for making the 96-well microplate carries with $1\times10^4$ cell/well HEK293T cells. Particularly, the HEK293T cells in the 96-well microplate are treated with a solution of composition for 24 hours and 48 hours, respectively. Moreover, the volume of the solution is at least 1.5 mg/mL, and an adult dosage of the composition in the solution is 3 mg/day/kg.

Figure 2:
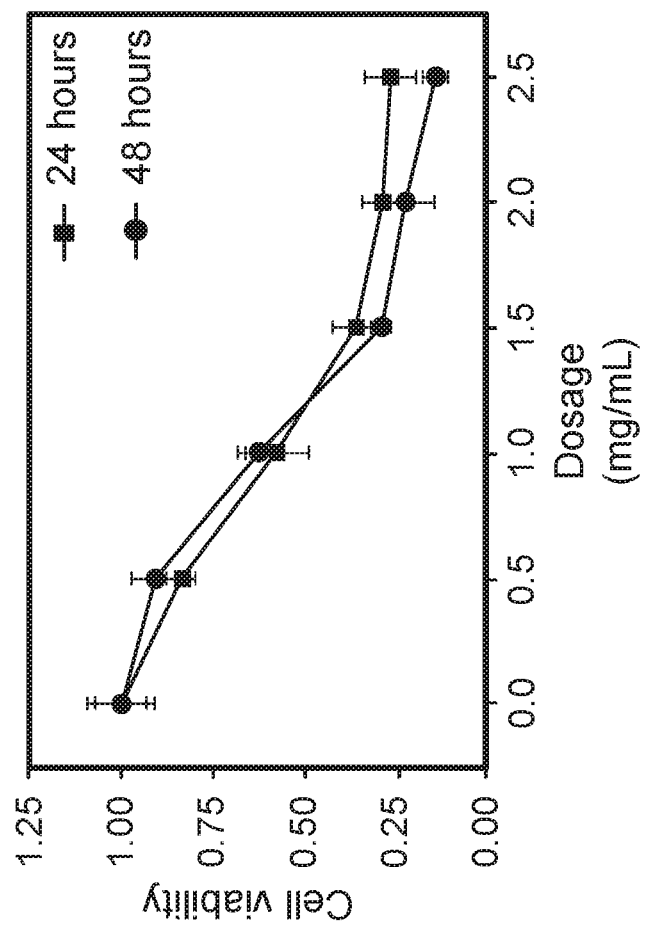
FIG. 2 shows two plot curve of dosage versus cell viability.

Please refer to FIG. 1, which illustrates two plot curves of dosage versus cell viability. Moreover, please simultaneously refer to FIG. 2, where two plot curves of dosage versus cell viability are provided. From the experimental data shown in FIG. 1 and FIG. 2, it can easily find that, after using the composition with different dosages to treat the HEK293T cells, the composition of at least 1.5 mg/mL is effectively inhibit the growth of HEK293T cell; moreover, the cell viability of the HEK293T cells is reduced to below 30% (15-30%). So that, the experimental data of FIG. 1 and FIG. 2 have proved that the composition proposed by the present invention indeed possesses the functionality to inhibit renal cancer cell growth.

Therefore, through above descriptions, the composition for inhibiting renal cancer cell growth and enhancing kidney function provided by the present invention has been introduced completely and clearly; in summary, the present invention includes the advantages of:

(1) Differing from the conventional therapeutics treating the glomerulonephritis by administering high-dosage steroid for 1-4 months, the renal function of a patient suffering with serious kidney failure can be obviously enhanced after administering the composition of 7 mg/day/kg to the patient for 20 days.

(2) Moreover, because the cell biological experiments have proved that the composition of the present invention possess the functionality to inhibit renal cancer cell growth, this novel composition can indeed be used with chemotherapy drugs clinically, so as to solve the issue that the chemotherapy drugs cannot effectively inhibit the renal cancer cell growth.

The above description is made on embodiments of the present invention. However, the embodiments are not intended to limit scope of the present invention, and all equivalent implementations or alterations within the spirit of the present invention still fall within the scope of the present invention.

What is claimed is:

1. A composition for inhibiting renal cancer cell growth and enhancing kidney function, comprising:
   an encapsulation layer, comprising:
   a water-soluble base material, comprising a polyethylene glycol (PEG) and a sodium stearate by a ratio of 9:1, and having a first weight percent in a range from 40 wt % to 60 wt %; and
   a plasticity-increasing base material, having a second weight percent in a range from 5 wt % to 10 wt %;
   an *Antrodia camphorata* extract, having a third weight percent in a range from 8 wt % to 15.5 wt %;
   a *Ganoderma lucidum* extract, having a fourth weight percent in a range from 18 wt % to 34 wt %; and
   a coenzyme, having a fifth weight percent in a range from 3.0 wt % to 6.2 wt %, wherein the coenzyme is a B vitamin group, a ubiquinone or a combination of the B vitamin group and the ubiquinone;
   wherein the composition is obtained by enclosing the *Antrodia camphorata* extract, the *Ganoderma lucidum* extract and the coenzyme with the encapsulation layer, and being further processed to a dripping pill with a pill size in a range from 2.0 mm to 3.5 mm.

2. The composition of claim 1, wherein the plasticity-increasing base material is selected from the group consisting of: pre-gelatinized starch, carboxymethyl starch, methylcellulose, sodium carboxymethyl cellulose, hydroxypropyl methylcellulose, acacia, alginic acid, dextrin, cyclodextrin, agar, lactose, and a combination thereof.

3. The composition of claim 1, wherein the *Antrodia camphorata* extract comprises triterpenoids and adenosine.

4. The composition of claim 1, wherein the *Ganoderma lucidum* extract comprises polysaccharides.

5. A method of treatment of kidney cancer by using a pharmaceutical composition, wherein the pharmaceutical composition comprises: an encapsulation layer made of a water-soluble base material of 40 wt % to 60 wt % and a plasticity-increasing base material of 5 wt % to 10 wt %, an *Antrodia camphorata* extract of 8 wt % to 15.5 wt %, a *Ganoderma lucidum* extract of 18 wt % to 34 wt %, and a coenzyme of 3.0 wt % to 6.2 wt %, and wherein the method comprises:

processing the pharmaceutical composition to a dripping pill with a pill size in a range from 2.0 mm to 3.5 mm and a pill weight in a range from 18 mg/pill to 25 mg/pill; and administering the dripping pill with an adult dosage of 7 mg/day/kg to a patient, thereby making a cell viability of human embryonic kidney cells 293T be reduced to below 30% as well as regulate blood urea nitrogen (BUN) and creatinine (Cr) of the patient.

6. The method of claim 5, wherein the coenzyme is a B vitamin group, a ubiquinone, or a combination of the B vitamin group and the ubiquinone.

7. The method of claim 5, wherein the water-soluble base material is selected from the group consisting of: polyethylene glycol (PEG), polyvinylpyrrolidone (PVP), polyoxyethylene monostearate (S40), sodium stearate, glycerin, gelatin, urea, poloxamer, and a combination thereof.

8. The method of claim 5, wherein the plasticity-increasing base material is selected from the group consisting of: pre-gelatinized starch, carboxymethyl starch, methylcellulose, sodium carboxymethyl cellulose, hydroxypropyl methylcellulose, acacia, alginic acid, dextrin, cyclodextrin, agar, lactose, and a combination thereof.

* * * * *